United States Patent
Kadavy et al.

(10) Patent No.: US 6,443,967 B1
(45) Date of Patent: Sep. 3, 2002

(54) INJECTION MOLDABLE FEEDSTOCK INCLUDING DIAMOND PARTICLES FOR ABRASIVE APPLICATIONS

(75) Inventors: Thomas D. Kadavy, Bellevue; Timothy J. Weaver, Duvall; Kevin Raudebaugh, Bellevue, all of WA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/848,761

(22) Filed: May 3, 2001

(51) Int. Cl.[7] .............................................. A61B 17/22
(52) U.S. Cl. ..................... 606/159; 606/80; 606/180
(58) Field of Search .................... 606/159, 180, 606/80; 451/541, 358, 61; 433/166

(56) References Cited

U.S. PATENT DOCUMENTS

| | | | | |
|---|---|---|---|---|
| 2,074,038 A | * | 3/1937 | Willey ........................ 219/149 |
| 2,534,127 A | * | 12/1950 | Howe | |
| 3,183,632 A | * | 5/1965 | Ferchland .................... 451/541 |
| 3,522,676 A | * | 8/1970 | Miller ......................... 264/332 |
| 5,312,427 A | * | 5/1994 | Shturman .................... 606/159 |
| 5,672,185 A | * | 9/1997 | Ryoke | |
| 5,885,149 A | * | 3/1999 | Gillet et al. .................. 125/15 |
| 5,895,397 A | * | 4/1999 | Jang et al. .................. 128/898 |
| 5,976,165 A | * | 11/1999 | Ball et al. ...................... 604/22 |
| 6,093,092 A | * | 7/2000 | Ramanath et al. .......... 451/527 |

* cited by examiner

Primary Examiner—Rodney M. Lindsey
(74) Attorney, Agent, or Firm—Christensen O'Connor Johnson Kindness PLLC

(57) ABSTRACT

A feedstock for creating cutting tools comprises a mixture of diamond particles, a binding material and a homogenizing agent that maintains the mixture of the diamond particles and binding material. In one present embodiment of the invention, the feedstock comprises diamond particles mixed with a binding agent of a brass powder and a wax or plastic homogenizing agent. The feedstock of the present invention is useful in making many types of abrasive cutting tools. One such cutting tool is an atherectomy burr for use in removing occlusions from a patient's blood vessel. A cutting tool made of the feedstock of the present invention has improved thermal conductivity compared with conventional atherectomy burrs.

6 Claims, 1 Drawing Sheet

INJECTION MOLDABLE FEEDSTOCK INCLUDING DIAMOND PARTICLES FOR ABRASIVE APPLICATIONS

FIELD OF THE INVENTION

The present invention relates to engineered materials for cutting applications and in particular to engineered materials for use in medical applications.

BACKGROUND OF THE INVENTION

In an effort to treat vascular diseases, a variety of minimally invasive, intravascular techniques have been developed. One technique, commonly used to treat vascular occlusions, is to utilize an abrasive burr that is routed within a vessel and rotated at high speed in order to ablate the occlusion. When plated with a relatively fine abrasive on the surface on the burr, the ablated particles are sufficiently small so that they are passed through the body without significant risk of downstream embolization.

The most common type of atherectomy burr comprises a metal bead that is plated with diamond particles. In general, such burrs can only be made in relatively simple shapes, such as ovoids and are relatively expensive to produce. Therefore, there is a need for a cost-effective method of making more complex shapes that might produce more efficient cutting surfaces.

Another problem with all current intravascular ablation techniques is the possibility of thermal damage caused by frictional heating at the treatment site. Such heating can damage healthy tissue at the site and may contribute to restenosis of a vessel. Therefore, there is a need for an ablation burr having improved thermal conductivity that will transfer heat away from a treatment site.

SUMMARY OF THE INVENTION

The present invention is an improved feedstock material from which abrasive cutting tools can be made. The material includes diamond particles, a binding material and a homogenizer that keeps the diamond particles and binding material mixed together. The combination of the diamond particles, binding material and homogenizer can be injection molded to create cutting devices of a variety of shapes and sizes. The proportions of the diamond particles and binding material can be adjusted in accordance with the desired application of the cutting tool.

The improved feedstock of the present invention can be used to manufacture industrial cutting tools as well as medical cutting tools. However, the feedstock is believed to be particularly advantageous in making medical cutting tools because of the high thermal conductivity of the diamond particles, which aids in the conduction of heat away from a cutting surface where the tool is used.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawing, wherein.

DETAILED DESCRIPTION OF THE PREFERRED EMBODIMENT

Figure 1:
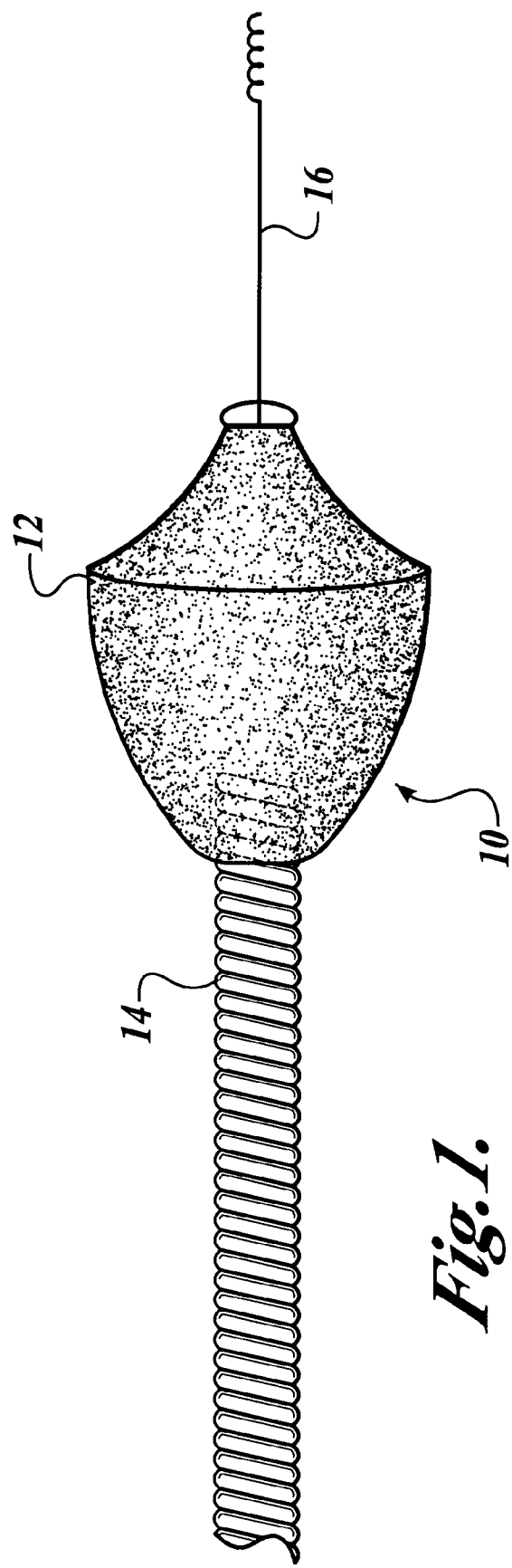
FIG. 1 illustrates a cutting tool in the form of an atherectomy burr made of a feedstock according to the present invention.

The present invention is an improved feedstock for use in manufacturing abrasive cutting tools. The feedstock comprises a mixture of diamond particles and one or more binding materials that hold the diamond particles together when the feedstock is sufficiently heated. Suitable binding materials include powders or granules of metals such as brass, titanium, ceramics, combinations thereof or other materials that have the ability to fuse the diamond particles into a solid mass. In addition, the binding material should be non-toxic if the cutting tool is to be used within the human body.

In addition, the feedstock material includes one or more homogenizing agents that operate to keep the diamond particles and binding material in a mixed state. Examples of a suitable homogenizing agents include plastics or waxes or other materials having the ability to keep the diamond particles and binding material in a mixed powder or liquid state.

To create an abrasive cutting tool from the feedstock, the feedstock is preferably placed into a mold and heated or otherwise treated to remove the one or more homogenizing agents from the mixture. Next, the binding material and diamond particles are heated such that the one or more binding materials fuse with the diamond particles contained therein.

Once the feedstock has been solidified during the injection molding process, additional processing can be done to create additional patterns or features within the molded part. For example, the molded cutting tool can be etched using photolithographic techniques to remove more of the binding material thereby further exposing more of the diamond particles in selected areas. Alternatively, the solid block containing diamond particles could be machined.

As will be appreciated, a relative percentage of the diamond particles with respect to the binding material may be varied in accordance with the desired application of the cutting tool. Similarly, the relative size of the diamond particles may also be selected in accordance with the desired cutting characteristics of the tool. In addition, the present invention allows cutting tools to be created with varying sizes of diamond particles by partially filling the injection molds with feedstocks having different diamond-to-binding material ratios or with different size diamond particles. For example, it may be desirable that a cardiac ablation burr have a more aggressive cutting surface towards its distal end and a less aggressive cutting surface towards its proximal end. Therefore, a feedstock having larger or more numerous diamond particles would be placed into that portion of the mold that creates the distal portion of the cutting tool while a feedstock having a less aggressive or fewer diamond particles in relation to the binding material can be used to fill up the portion of the mold corresponding to the proximal end of the ablation burr.

As indicated above, one specific application for the feedstock of the present invention is to manufacture atherectomy burrs useful for removing occlusions within a patient's blood vessel. As shown in FIG. 1, a cutting tool 12 that is formed as an atherectomy burr is adapted to be secured to a driveshaft 14. The cutting tool 12 preferably has a lumen extending therethrough so that the cutting tool can be routed over a guide wire 16. The driveshaft 14 is rotated by a source of rotational motion such as a turbine or electric motor. When rotated, the cutting tool 12 removes deposits in a patient's vessel.

An atherectomy burr made of the feedstock of the present invention is believed to have advantages over traditional atherectomy burrs due to the high thermal conductivity of the diamond particles versus the thermal conductivity of traditional ablation burr materials such as brass coated with diamonds. Therefore, it is anticipated that atherectomy burrs made of the feedstock described above will have a greater ability to transfer heat away from an ablation site thereby reducing the likelihood of thermal damage as a result of an atherectomy procedure.

In addition, the feedstock of the present invention can be used to create other abrasive cutting tools for non-medical applications using conventional molding or machining techniques known to those of ordinary skill in the art.

While the present invention has been disclosed with respect to its currently preferred embodiment, those skilled in the art will recognize that changes may be made without departing from the scope of the invention. It is therefore intended that the scope of the present invention be determined from the following claims and equivalents thereto.

The embodiments of the invention in which an exclusive property or privilege is claimed are defined as follows:

1. An atherectomy burr for removing deposits in a patient's blood vessel comprising:
   a burr body made of a feedstock that is comprised of a mixture of diamond particles, a binding material and a homogenizing agent, the burr body being adapted to be secured to and rotated by a driveshaft, wherein the burr body has an abrasive outer surface to remove deposits in the vessel when rotated by the driveshaft.

2. An atherectomy burr, comprising:
   a burr body adapted to be coupled to a driveshaft that is rotated in a patient's vessel to remove an occlusion, the burr body being made of diamond particles that are combined with a binding material that holds the diamond particles in a solid form.

3. An atherectomy buff comprising:
   a burr body adapted to be coupled to a driveshaft that is rotated in a patient's blood vessel, the burr body being made of diamond particles and a binding means for forming the diamond particles into a solid, the burr body having an abrasive outer surface that removes the deposits in a vessel when rotated by the driveshaft.

4. The atherectomy burr of claim 3, wherein the burr body has a pattern that is etched onto the outer surface of the burr, wherein the pattern selectively removes a portion of the binding means on the outer surface of the burr.

5. An atherectomy burr for removing deposits from a vessel, including:
   a burr body having an abrasive outer surface, the burr body being coupled to a drive shaft and rotated in a vessel to remove deposits:
      the burr body having a thermally conductive composite for removing heat from the site at which deposits are removed from the vessel.

6. The atherectomy burr of claim 5, wherein the thermally conductive composite comprises a composite of diamond particles and a binding material.

* * * * *

UNITED STATES PATENT AND TRADEMARK OFFICE
CERTIFICATE OF CORRECTION

PATENT NO. : 6,443,967 B1  Page 1 of 1
DATED : September 3, 2002
INVENTOR(S) : T.D. Kadavy et al.

It is certified that error appears in the above-identified patent and that said Letters Patent is hereby corrected as shown below:

Column 4,
Line 4, "buff" should read -- burr --

Signed and Sealed this

Eighth Day of April, 2003

JAMES E. ROGAN
*Director of the United States Patent and Trademark Office*